(12) United States Patent
Prakash et al.

(10) Patent No.: US 8,340,750 B2
(45) Date of Patent: Dec. 25, 2012

(54) MECHANICAL FUNCTION MARKER CHANNEL FOR CARDIAC MONITORING AND THERAPY CONTROL

(75) Inventors: Rajan Prakash, St. Louis Park, MN (US); Sameh Sowelam, Maple Grove, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 894 days.

(21) Appl. No.: 11/780,140

(22) Filed: Jul. 19, 2007

(65) Prior Publication Data

US 2009/0024045 A1    Jan. 22, 2009

(51) Int. Cl.
*A61B 5/00*    (2006.01)
(52) U.S. Cl. ........................................ 600/523; 600/509
(58) Field of Classification Search .......... 600/508–509, 600/522–523
See application file for complete search history.

(56) References Cited

U.S. PATENT DOCUMENTS

| | | | |
|---|---|---|---|
| 4,374,382 A | 2/1983 | Markowitz | |
| 5,413,593 A | 5/1995 | Spinelli et al. | |
| 5,549,654 A | 8/1996 | Powell | |
| 5,720,771 A | 2/1998 | Snell | |
| 5,836,987 A * | 11/1998 | Baumann et al. | 607/17 |
| 6,795,734 B2 | 9/2004 | Vanderlinde et al. | |
| 7,031,764 B2 | 4/2006 | Schwartz et al. | |
| 7,308,311 B2 * | 12/2007 | Sorensen et al. | 607/32 |
| 7,778,699 B1 * | 8/2010 | Ferrise et al. | 600/523 |
| 2004/0167410 A1 * | 8/2004 | Hettrick | 600/486 |
| 2004/0172079 A1 * | 9/2004 | Chinchoy | 607/17 |
| 2004/0186524 A1 * | 9/2004 | Chinchoy | 607/17 |
| 2006/0047216 A1 | 3/2006 | Dorr et al. | |
| 2006/0149184 A1 | 7/2006 | Soykan et al. | |
| 2006/0195151 A1 | 8/2006 | Vanderlinde | |

OTHER PUBLICATIONS

International Search Report, PCT/US2008/068343, Jan. 10, 2008, 6 Pages.

* cited by examiner

*Primary Examiner* — Carl H Layno
*Assistant Examiner* — Paula J Stice
(74) *Attorney, Agent, or Firm* — Evans M. Mburu

(57) ABSTRACT

The implantable medical device (IMD) system disclosed here utilizes one or more cardiac sensors that measure mechanical characteristics of the heart, such as left ventricular acceleration or right ventricular pressure. The raw sensor data is collected and processed by the IMD, which derives one or more mechanical event marker signals from features, traits, and characteristics of the sensor data waveforms. The mechanical event marker signals are wirelessly transmitted to an external monitor device for display.

38 Claims, 6 Drawing Sheets

MECHANICAL FUNCTION MARKER CHANNEL FOR CARDIAC MONITORING AND THERAPY CONTROL

TECHNICAL FIELD

Embodiments of the subject matter described herein relate generally to implantable medical device systems. More particularly, embodiments of the subject matter relate to a marker channel associated with the implantable medical device.

BACKGROUND

Physiological data can be challenging to obtain, especially when such data relates to the health, operation, and other characteristics of the heart. Cardiac data is commonly obtained through the use of electrocardiograms (ECGs) and/or myocardiograms. Obtaining cardiac data often requires invasive procedures such as catheterization (which involves the acute placement of sensors) and/or the use of imaging techniques such as echocardiography or magnetic resonance imaging (MRI). Acquiring cardiac information via imaging is expensive, time consuming, and resource exhausting.

Implantable medical devices (IMDs) are well known in the medical device field and are known to monitor heart activity, provide pacing therapy, and/or provide defibrillation therapy. In this regard, IMDs can be used to collect physiological data directly from the heart. IMDs commonly employ sensor/electrode leads that obtain electrogram (EGM) readings from heart tissue and/or deliver electrical therapy to the heart tissue as needed. Moreover, IMDs are often designed to support wireless data communication (telemetry) with external devices, e.g., IMD programmers or patient monitors.

EGM or ECG data can be used to evaluate the condition of the heart. At least one known IMD system utilizes an EGM-based electrical marker channel to indicate the occurrence of certain cardiac electrical events such as sensed and paced events associated with the operation of a pacemaker device. The electrical marker channel is derived at least in part from the EGM signal, and the electrical marker channel identifies the occurrence of events such as: ventricular pacing; atrial sensing; atrial refractory sensing; ventricular sensing; and ventricular refractory sensing. Accordingly, electrical marker channels are effective at identifying events that are directly related to sensed electrical activity within the heart. However, electrical marker channels do not convey cardiac information related to chemical or mechanical phenomena.

BRIEF SUMMARY

The IMD, IMD system, and related operating methods described herein collect mechanical-based cardiac sensor data and generate or derive cardiac event marker signals from the sensor data. A sensor utilized by the IMD system can be an intra-cardiac sensor, a sensor that is located in the thoracic cavity, or more broadly a sensor that is located elsewhere in the body or on the body surface. The mechanical-based event marker signals can be transmitted to an external device for display, processing or other usage.

The above and other aspects may be carried out by an embodiment of an operating method for an IMD configured for implanted operation in the body of a patient. The method is used to obtain information related to the cardiac cycle of the patient. The method involves: receiving a physiological data signal from a mechanical characteristic sensor, where the physiological data signal is indicative of mechanical cardiac functionality of the patient; deriving cardiac event markers for the patient from attributes of the physiological data signal; and generating a cardiac event marker signal using the cardiac event markers, the cardiac event marker signal identifying cardiac cycle timing characteristics for the patient.

The above and other features may be carried out by an embodiment of an IMD configured for implanted operation in the body of a patient. The IMD includes: a data collection module configured to obtain a physiological data signal indicative of mechanical cardiac functionality of the patient; a data processing module coupled to the data collection module, the data processing module being configured to derive cardiac event markers for the patient from attributes of the physiological data signal, and to generate a cardiac event marker signal using the cardiac event markers, the cardiac event marker signal identifying cardiac cycle timing characteristics for the patient; and a communication module coupled to the data processing module, the communication module being configured to transmit the cardiac event marker signal to a device external to the IMD.

The above and other features may also be carried out by an embodiment of an IMD system having an IMD, a mechanical characteristic sensor in communication with the IMD, and a monitor device in communication with the IMD. The IMD includes: a data collection module configured to obtain a physiological data signal indicative of mechanical cardiac functionality of the patient; a data processing module coupled to the data collection module, the data processing module being configured to derive cardiac event markers for the patient from attributes of the physiological data signal, and to generate a cardiac event marker signal using the cardiac event markers, the cardiac event marker signal identifying cardiac cycle timing characteristics for the patient; and a communication module coupled to the data processing module, the communication module being configured to transmit the cardiac event marker signal to devices external to the IMD. The mechanical characteristic sensor is configured to generate the physiological data signal in response to mechanical cardiac phenomena, and the monitor device is configured to receive the cardiac event marker signal from the communication module. The monitor device is also configured to display a graphical representation of the cardiac event marker signal.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is illustrative in nature and is not intended to limit the embodiments of the invention or the application and uses of such embodiments. Furthermore, there is no intention to be bound by any expressed or implied theory presented in the preceding technical field, background, brief summary or the following detailed description.

Techniques and technologies may be described herein in terms of functional and/or logical block components and various processing steps. It should be appreciated that such block components may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments may be practiced in conjunction with any number of IMD configurations, medical device therapies, and monitoring/diagnostic equipment, and that the system described herein is merely one suitable example.

For the sake of brevity, conventional techniques related to IMD sensor signal processing, ventricular/atrial pressure sensing, accelerometers, wireless telemetry, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the subject matter.

Figure 1:
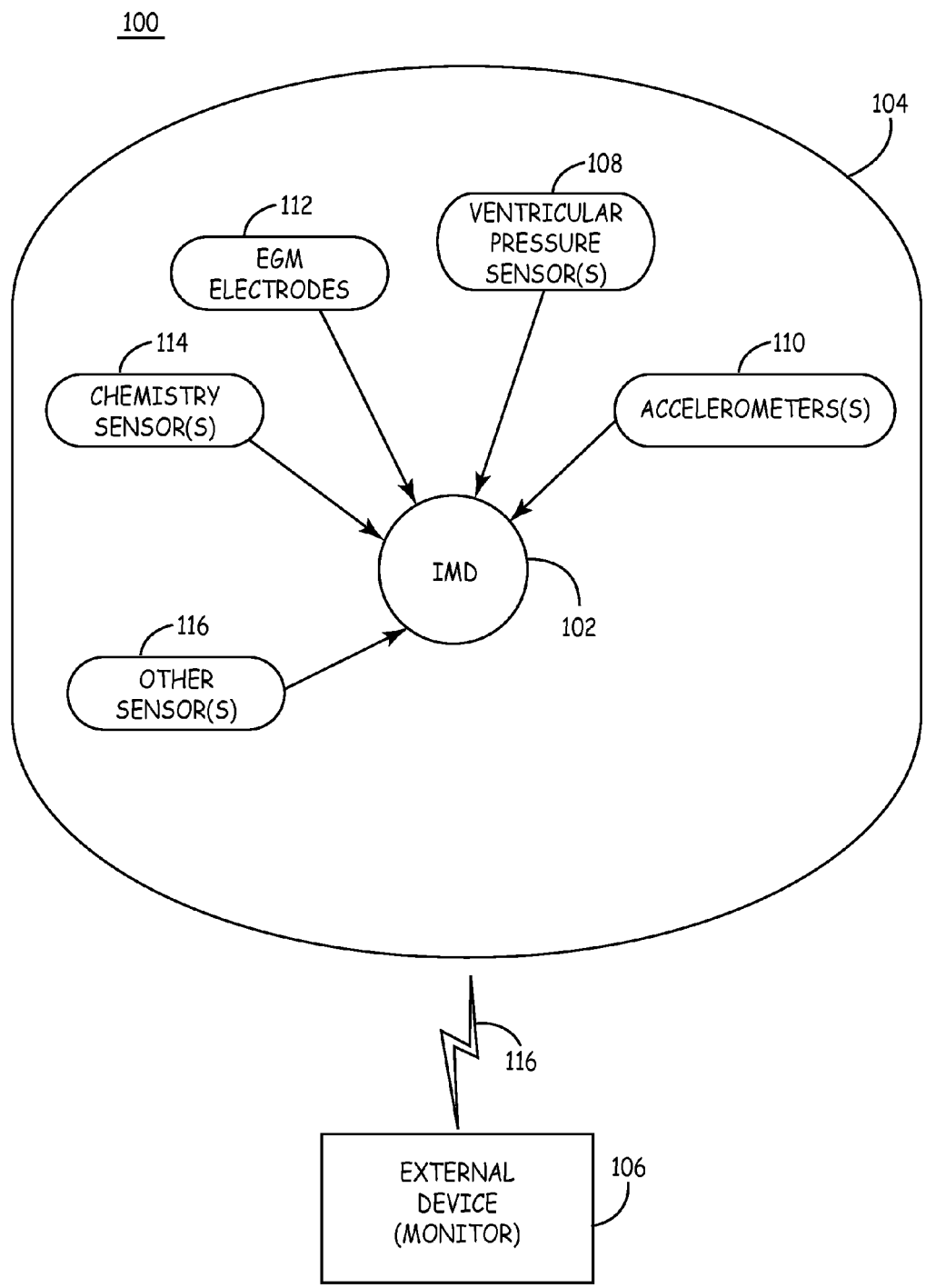
FIG. 1 is a schematic representation of an embodiment of an IMD system.
Figure 2:
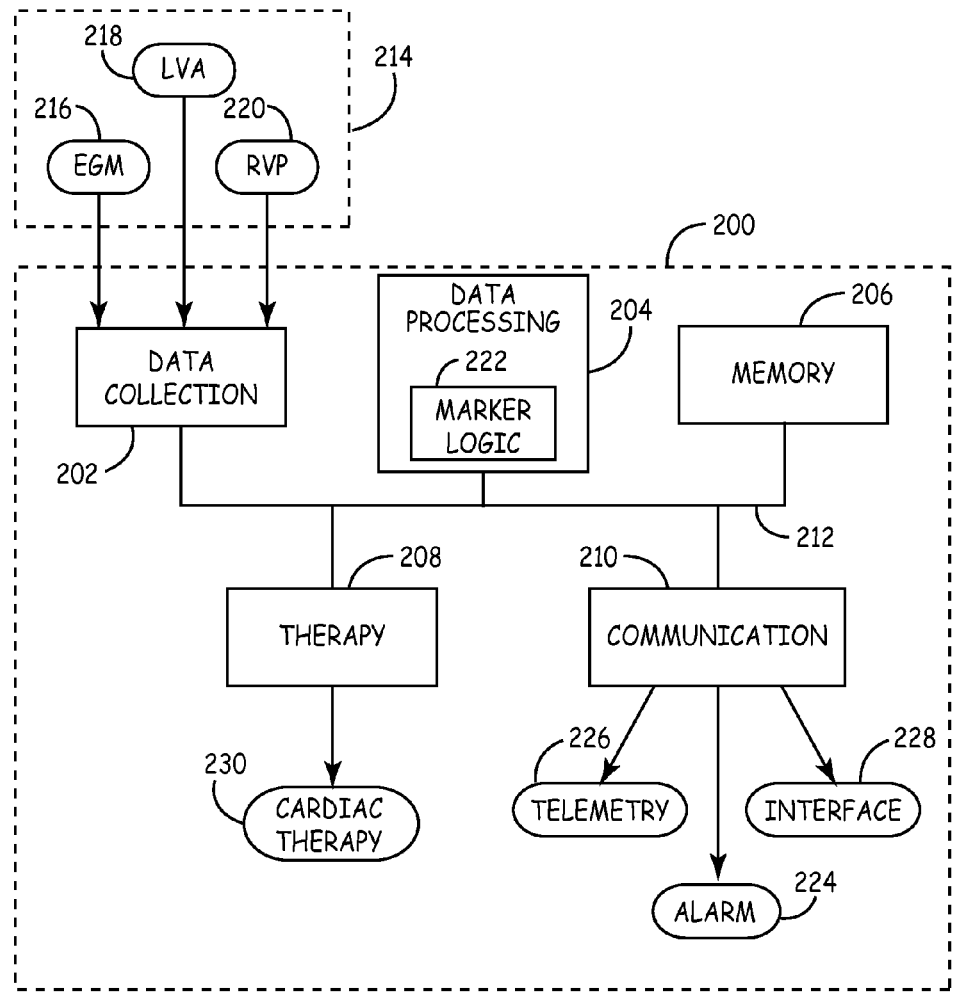
FIG. 2 is a schematic representation of a portion of an IMD suitable for use in the IMD system shown in FIG. 1.

The following description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in FIG. 1 and FIG. 2 depict exemplary arrangements of elements, additional intervening elements, devices, features, or components may be present in an embodiment of the depicted subject matter.

The system embodiments may be described herein with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the systems described herein (which may reside at an IMD, an external monitor device, or elsewhere in the system environment) are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links.

Although invasive procedures and/or imaging are the preferred means for obtaining some cardiac diagnostics, certain other measures might be obtained using implanted sensors. In this regard, different types of physiological sensors (e.g., chemical sensors, mechanical sensors, microphones or other audio transducers, or optical sensors) can be utilized in connection with cardiac IMD devices, where the additional sensors supplement conventional EGM sensors. For example, accelerometer and pressure sensors with high resolution capability are capable of divulging information within each cardiac cycle. Cardiac events within different chambers of the heart can be sensed and displayed as a mechanical-based marker channel for the patient or a caregiver. This feature could be added to existing IMDs and associated programmer software.

Physicians can order/procure an acute (on demand) test using the device programmer or via patient networks. Moreover, cardiac disease management can be enhanced with existing patient care management systems and remote network-based diagnostic systems. Physicians could activate the different sensors simultaneously and interpret the signals relative to each other (in a manner akin to interpreting an EGM or ECG). Physicians may, for example, obtain physiological information that would otherwise require an echocardiographic study. Consequently, the use of additional sensor types in IMD applications might also prove beneficial in terms of reducing imaging costs involved with patient and disease management.

The embodiments described herein utilize a physiologic cardiac event marker channel that corresponds to a signal representing the different phases of the cardiac cycle. The physiologic marker channel is analogous to an electrical marker channel but it identifies the timings of different phases (such as ejection, isovolumic contraction, and isovolumic relaxation) detected in the cardiac cycle using mechanical-based, chemical-based, and/or other sensor types that can be used to derive a mechanical function marker channel. The marker channel can convey mechanical events (timing), duration, magnitude, and other characteristics of cardiac/physiologic function derived from a signal or a combination of signals received or derived from sensor(s) in the manner described here. In this context, a received signal is a signal generated by a sensor, e.g., an accelerometer signal or a pressure signal, while a derived signal is a signal derived or calculated from one or more received signals. For instance, a derived signal may be produced using some form of averaging, signal processing, mathematical operation, or the like.

The specific details of the physiologic marker channel can be determined for each device based on the sensors it incorporates. The physiologic marker channel can potentially display timings of sensor discernable cardiac events and the magnitudes of important physiologic parameters that the sensor is capable of measuring. For background reference, a system that generates an electrical marker channel is disclosed in U.S. Pat. No. 4,374,382, the relevant content of which is incorporated by reference herein.

In accordance with certain embodiments, an accelerometer and/or a ventricular pressure sensor are used to measure cardiac performance characteristics, and the sensor data is processed to generate the physiologic marker channel. Alternatively or additionally, a system embodiment utilizes one or more chemical-based sensors, e.g., sensors that measure potassium, pH, oxygen, carbon dioxide, or other blood chemistry. Consequently, an IMD system can merge information obtained from a variety of physiologic sensors (including EGM sensors) to display progressively more accurate cardiac information. Alternatively or additionally, a system embodiment utilizes one or more other sensors that measure characteristics from which cardiac information and a mechanical function marker channel can be derived. These alternate sensor types include, without limitation: microphones or other audio transducers; optical sensors; etc.

Similar to the manner in which electrical cardiac information is sensed from the acquired EGMs in IMDs and displayed as an electrical marker channel, the introduction of mechanical-based (and/or chemical-based) sensors makes it possible to provide additional cardiac performance details as well as specific timings of the valve closings, contraction and relaxation periods, etc., in a basic representation as a physiologic marker channel. Ventricular hemodynamic performances could be measured and displayed as well. The use of different sensor technologies, such as an accelerometer located in the left ventricle, allows the system to provide left ventricular diagnostic information and other information related to ventricular event timing, where such information is added on to the physiologic marker channel. Moreover, the physiologic marker channel can be superimposed on the electric marker channel, resulting in a combination that can be used as a tool by the physician to diagnose the patient or adjust therapy for the patient.

Referring now to the drawings, FIG. 1 is a schematic representation of an embodiment of an IMD system 100. This generalized embodiment includes an IMD 102 configured for implanted operation in the body 104 of a patient, an external monitor device 106 in communication with IMD 102, and at least one implanted physiological characteristic sensor in communication with IMD 102. In certain embodiments, a physiological characteristic sensor is a mechanical characteristic sensor that is configured to generate a physiological data signal in response to mechanical cardiac phenomena. For example, IMD system 100 is shown with the following types of mechanical characteristic sensors: ventricular pressure sensor(s) 108 and accelerometer(s) 110. IMD system 100 is also shown with a common type of electrical characteristic sensor, namely, electrogram (EGM) electrodes 112. Furthermore, particular embodiments of IMD system 100 include chemistry sensor(s) 114, which are configured to measure chemical characteristics of body fluids such as oxygen levels, pH levels, potassium levels, glucose levels, or the like. An embodiment of IMD system 100 may alternatively or additionally include one or more other sensors or measurement devices 116, e.g., a microphone or other audio transducer, an optical sensor, a timer, a motion sensor, a deflection sensor, an ultrasonic sensor, or a flow meter.

For the application described here, an accelerometer 110 is suitably configured to measure acceleration of a heart wall of the patient, and to provide a heart wall acceleration signal to IMD 102. In practice, accelerometer 110 is located at the end of a single lead that is coupled to IMD 102 (the lead could be realized as a distinct lead devoted to accelerometer 110 or as a combined lead that also serves as a lead for a monitor, pacing, or other function). The end of the lead (and, therefore, accelerometer 110) is affixed to the desired heart wall, such as the posterior lateral left ventricle wall. Alternatively, accelerometer 110 is configured as a standalone device that transmits the acceleration data to IMD 102 via a wireless link. In this manner, accelerometer 110 measures the acceleration of the respective heart wall and IMD 102 can utilize the acceleration data as described in more detail below.

For the application described here, a pressure sensor (such as ventricular pressure sensor 108) is suitably configured to measure pressure within a heart chamber of the patient, and to provide a heart chamber pressure signal to IMD 102. In practice, pressure sensor 108 is located at the end of a single lead that is coupled to IMD 102 (the lead could be realized as a distinct lead devoted to pressure sensor 108 or as a combined lead that also serves as a lead for a monitor, pacing, or other function). The end of the lead (and, therefore, pressure sensor 108) is located within the desired heart chamber, such as the right ventricle. Alternatively, pressure sensor 108 is configured as a standalone device that transmits the pressure data to IMD 102 via a wireless link. Thus, pressure sensor 108 measures the pressure in the respective heart chamber and IMD 102 can utilize the pressure data as described in more detail below.

IMD 102 may also be configured to obtain an EGM signal from EGM electrodes 112. EGM electrodes 112 represent electrical sense electrodes that detect electrical activity of the heart in a conventional manner. In practice, EGM electrodes 112 are located at the ends of leads coupled to IMD 102 (the leads could be realized as a distinct leads devoted to EGM electrodes 112 or as combined leads that also serve as leads for a monitor, pacing, or other function). Alternatively, EGM electrodes 112 may be utilized with a standalone device that transmits the EGM data to IMD 102 via a wireless link. Accordingly, EGM electrodes 112 are utilized to provide the EGM signal to IMD 102, which in turn can utilize the EGM data as described in more detail below.

IMD 102 may also leverage chemical characteristic data and/or other data obtained from chemistry sensors 114 and other sensors 116 in an analogous manner to that described below. The embodiment of IMD system 100 described here need not employ chemistry sensors 114 or other sensors 116 and, therefore, such chemistry sensors 114 and other sensors 116 will not be addressed in detail herein.

IMD 102 is suitably configured to transmit information to external devices such as external monitor device 106 via one or more wireless telemetry links 116. The transmitted information, signals, and data may include or convey physiological patient data (e.g., data collected by IMD 102), status data associated with the operation of IMD 102 or any implanted sensors, signaling data, or the like. In this manner, external monitor device 106 can acquire the EGM signal for the patient and display a graphical representation of the EGM signal as needed. As described in more detail below, external monitor device 106 is also suitably configured to receive a cardiac event marker signal from IMD 102, which can be displayed in conjunction with the EGM signal.

FIG. 2 is a schematic representation of an embodiment of a portion of an IMD suitable for use in IMD system 100. In particular, FIG. 2 depicts an exemplary data processing layout for an IMD processor architecture 200, which may be located within the housing of an IMD as described herein. In this example, processor architecture 200 includes, without limitation: a data collection module 202, a data processing module 204, a suitable amount of memory 206, a therapy module 208, and a communication module 210. These modules may be coupled to each other via a suitable data communication bus or arrangement 212. Each of the various modules may be implemented with computer-executable instructions stored in memory 206 and executing on processor architecture 200, or in any other practical manner. The exemplary modules and blocks shown in FIG. 2 are intended to illustrate one logical model for implementing an embodiment of an IMD, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

Data collection module 202 suitably interacts with one or more data sources 214 to obtain data about the patient, conveyed by one or more physiological data signals. Data sources 214 include any source of information about the patient's heart, and possibly other physiologic information. In particular embodiments, data collection module 202 obtains one or more physiological data signals that are indicative of mechanical cardiac functionality of the patient. In other words, these physiological data signals indicate mechanical (rather than electrical or chemical) characteristics of the patient's heart. In certain embodiments, data sources 214 may include an EGM source 216 (such as EGM electrodes or sensors) that provides electrical impulses or other observed signals that can be used to model the patient's EGM waveform. Other data sources 214 may include a left ventricular accelerometer (LVA) 218 and a right ventricular pressure (RVP) sensor 220. As mentioned above in connection with IMD system 100, an IMD may utilize alternative or additional sensors, such as a sensor for determining cardiac conduction time, temperature sensors, blood pH sensors, and/or other known data sources. The various data sources 214 may be provided alone or in any combination with each other, and may vary widely from embodiment to embodiment. Moreover, a given sensor may be an intra-cardiac sensor, a sensor in the thoracic cavity, or a sensor located elsewhere in or on the body of the patient.

LVA sensor 218 is suitably configured to measure the real-time acceleration of the left ventricle wall and to provide raw heart wall acceleration data to data collection module 202. In turn, data collection module 202 and/or data processing module 204 can convert the raw acceleration data into a usable LVA signal for analysis as described herein. A practical IMD can utilize any suitable LVA sensor 218, including, without limitation: LVA sensors that are mounted through the atrial septal wall of the heart; and LVA sensors that are inserted through the left atrial appendage or anterior posterior or lateral appendage, or through the mitral valve or via the coronary veins. A sensor could be embedded epicardially by surgical means or transvenous placement on the epicardial/midmyocardial region or placed endocardially through left atrial appendage or other means. Alternatively, a sensor could be located at the tip of a lead. Indeed, processor architecture 200 can be configured to accommodate the specific LVA signal format and characteristics associated with the particular LVA sensor 218 or sensors deployed with the IMD.

RVP sensor 220 is suitably configured to measure the real-time RVP of the patient's heart and to provide raw RVP data to data collection module 202. In turn, data collection module 202 and/or data processing module 204 can convert the raw RVP data into a usable RVP signal for analysis as described herein. Processor architecture 200 can be configured to accommodate the specific RVP signal format and characteristics associated with the particular RVP sensor 220 or sensors deployed with the IMD. Notably, a pressure sensor utilized by an IMD system as described here can be located in any chamber, wall, or vein of the heart, or in the systemic side of the vasculature.

Data collection module 202 suitably receives data from each of the data sources 214 by polling each of the data sources 214, by responding to interrupts or other signals generated by the data sources 214, by receiving data at regular time intervals, or according to any other temporal scheme. In this embodiment, data collection module 202 can obtain an EGM signal, an LVA signal, and/or an RVP signal from the patient for processing. Data may be received at data collection module 202 in digital or analog format according to any protocol. If any of the data sources 214 generate analog data, data collection module 202 suitably translates the analog signals to digital equivalents using any form of analog-to-digital conversion scheme presently known or subsequently developed. Data collection module 202 may also convert data from protocols used by data sources 214 to data formats acceptable to data processing module 204, as appropriate.

Figure 6:
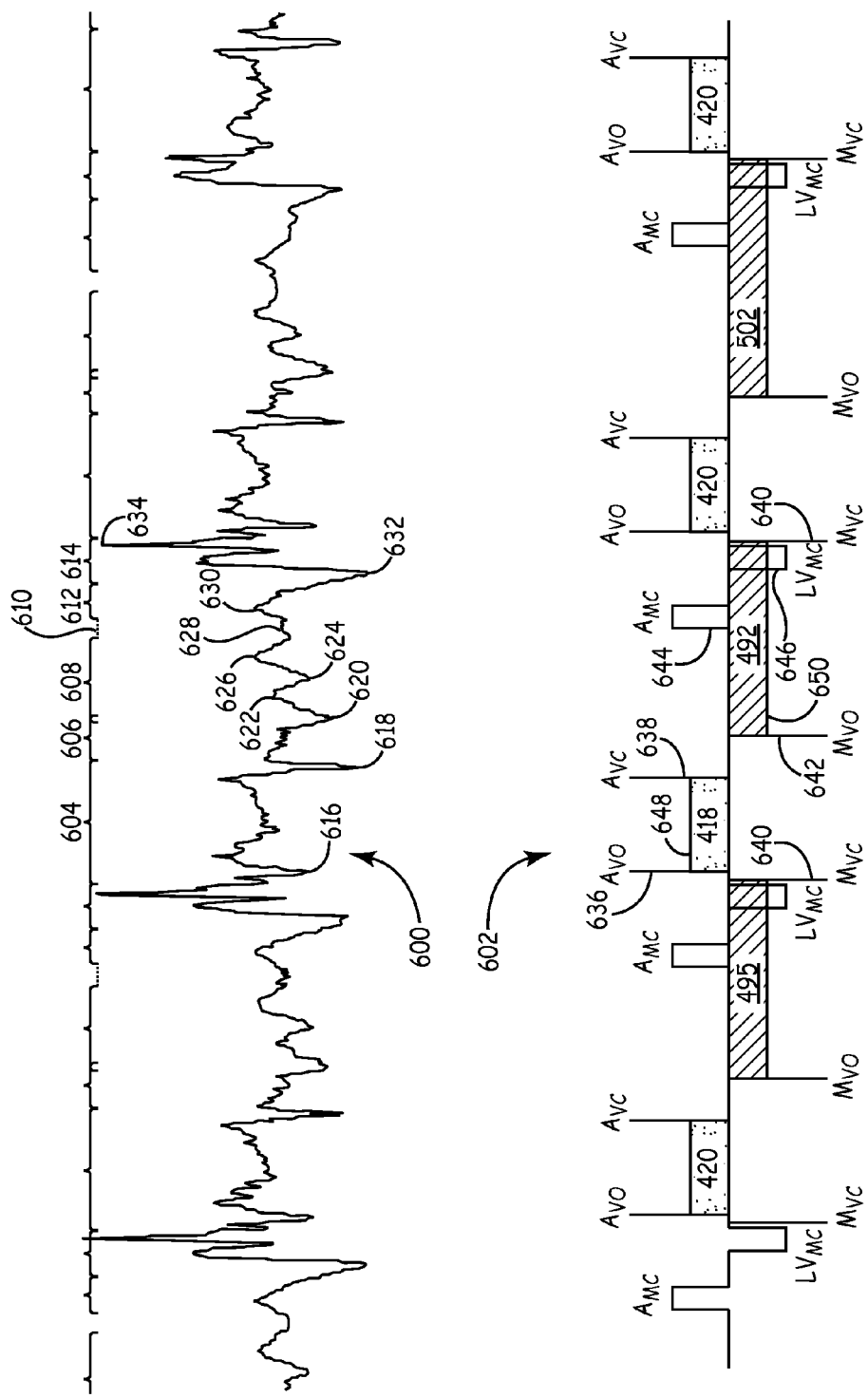
FIG. 6 is a diagram that depicts a left ventricle acceleration signal and a corresponding mechanical function marker signal.

Data processing module 204 is any circuit, programming routine, application or other hardware/software module that is capable of processing data received from data collection module 202. In various embodiments, data processing module 204 is a software application executing on processor architecture 200 to implement the processes described below. Accordingly, data processing module 204 interprets received EGM signals, LVA signals, and/or RVP signals, generates or analyzes signals based upon or derived from the received signals, and/or handles other data to generate one or more cardiac event marker signals from the raw physiological sensor data. Data processing module 204 may utilize suitably configured marker logic 222 to analyze the sensor data signals, identify the event markers, and generate the event marker signals. In this regard, marker logic 222 derives cardiac event markers for the patient from attributes of one or more physiological data signals and generates cardiac event marker signal(s) using the derived event markers. A cardiac event marker signal is formatted such that it identifies cardiac cycle timing characteristics for the patient. An exemplary cardiac event marker signal corresponding to an LVA signal is depicted in FIG. 6.

In an exemplary embodiment, data processing module 204 receives the sensor signals and/or other appropriate information from data collection module 202 and interprets the sensor data using appropriate digital signal processing techniques. For example, data processing module 204 may generate a secondary signal that is based upon the first derivative of the RVP signal (such a secondary signal may be referred to herein as a dRVP/dt signal).

As described in more detail below, data processing module 204 is configured to identify at least one attribute of the LVA signal, at least one attribute of the RVP signal, and/or at least one attribute of the dRVP/dt signal by analyzing waveform characteristics of the sensor signals, e.g., occurrences of peaks and valleys, excursions above and below a reference level, and/or curvature of the signals. In particular, cyclical attributes can be correlated to certain cardiac cycle events. Accordingly, certain attributes of the LVA signal can be analyzed to derive cardiac event markers such as, without limitation: atrial mechanical contraction event markers; aortic valve opening event markers; aortic valve closing event markers; left ventricular mechanical contraction event markers; mitral valve opening event markers; and mitral valve closing event markers. Moreover, certain attributes of the RVP signal (or the dRVP/dt signal) can be analyzed to derive other cardiac event markers such as, without limitation: pre-ejection interval event markers; systolic time interval event markers; ejection time interval event markers; and estimated pulmonary artery diastolic pressure event markers. In practice, a given event marker may be derived from attributes of more than one raw sensor signal. For example, certain cardiac event markers can be derived from attributes of the RVP signal and attributes of an EGM signal. The event markers are utilized to form cardiac marker signals that convey the timing characteristics of the cardiac events.

Communication module 210 is any circuit or routine that facilitates the transfer of data, information, reports, or programming instructions between the IMD and an external device, system, or person (e.g., the patient, a physician, or a caregiver). In various embodiments, communication module 210 may be configured to generate an audible or visible alarm 224, handle wireless messages via a telemetry circuit 226, or manage the transmission of other data using any suitable interface 228. In certain embodiments, communication module 210 and telemetry circuit 226 cooperate to transmit cardiac event marker signals to devices external to the IMD, such as an external monitor device 106 (FIG. 1). In turn, external monitor device 106 receives the cardiac event marker signal and displays a graphical representation of the marker signal for viewing by the user. In certain embodiments the external monitor device 106 is configured to acquire an EGM/ECG signal for the patient, and to display a graphical representation of the EGM/ECG signal concurrently with the display of the marker signal, using a common time axis. This enables the user to visually compare characteristics of the EGM/ECG signal to characteristics of the marker signal. External monitor device 106 may acquire an EGM signal from the IMD via telemetry circuit 226 or from another piece of external equipment.

Therapy module 208 is any circuit, software application or other component that is configured to deliver cardiac therapy 230 to the patient. Some IMDs, such as a sensing or monitoring IMD, do not utilize therapy module 208. In the illustrated embodiment, therapy module 208 might be configured to provide dual-chamber pacing therapy as one form of cardiac therapy 230. In some embodiments, therapy module 208 may be alternatively or additionally configured to deliver other modes of pacing, post-extrasystolic potentiation, cardioversion, defibrillation and/or any other therapy.

The various components and processing modules of the IMD may be housed in a common housing or can. Alternatively, portions of the IMD may be housed separately. For example, portions of therapy module 208 could be integrated with the IMD or provided in a separate housing. In this case, therapy module 208 may interact with therapy electrodes via an electrical cable, wireless link, or interface 228.

Figure 3:
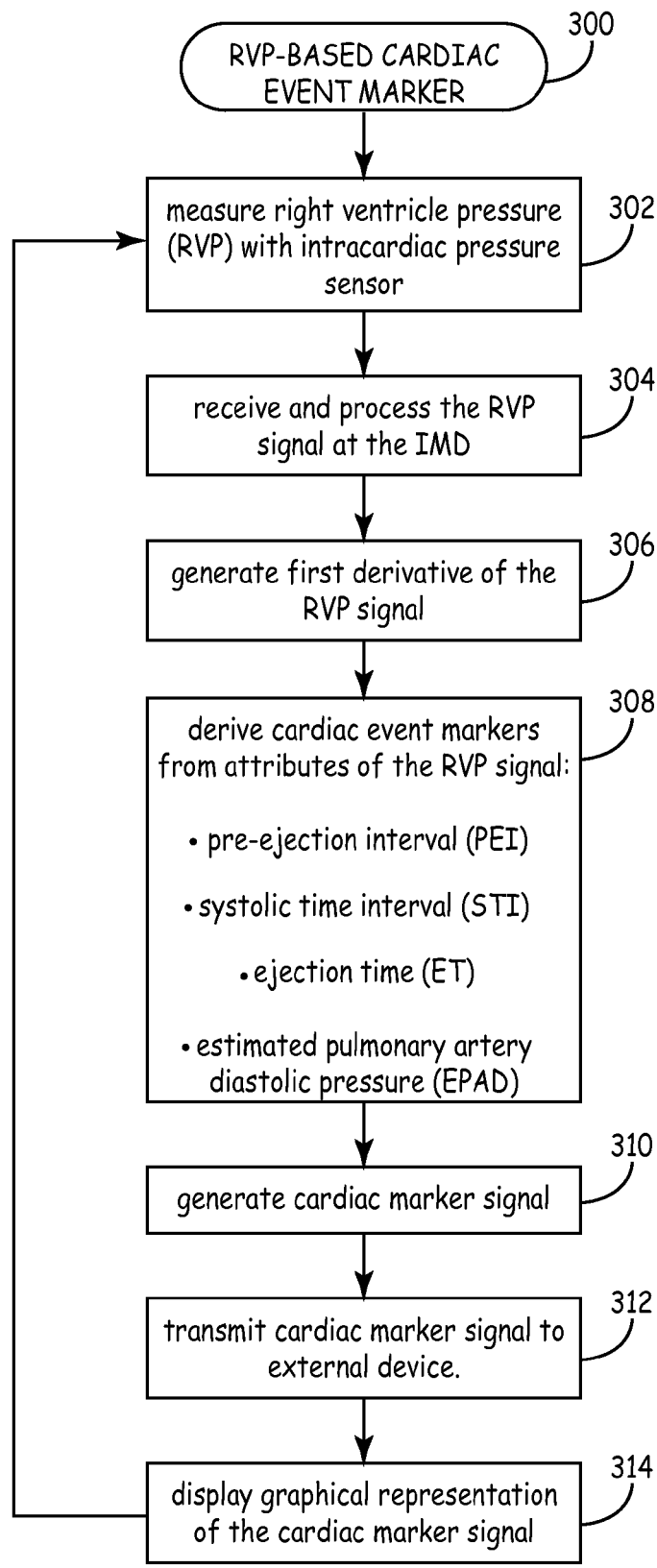
FIG. 3 is a flow chart that illustrates an embodiment of a cardiac event marker process that utilizes right ventricle pressure data.

FIG. 3 is a flow chart that illustrates an embodiment of a cardiac event marker process 300 that utilizes right ventricle pressure data. The various tasks performed in connection with process 300 may be performed by software, hardware, firmware, or any combination thereof. For illustrative purposes, the following description of process 300 may refer to elements mentioned above in connection with FIG. 1 and FIG. 2. In practice, portions of process 300 may be performed by different elements of the described system, e.g., implanted sensors, an IMD, or an external monitoring device. It should be appreciated that process 300 may include any number of additional or alternative tasks, the tasks shown in FIG. 3 need not be performed in the illustrated order, and process 300 may be incorporated into a more comprehensive procedure or process having additional functionality not described in detail herein.

Figure 4:
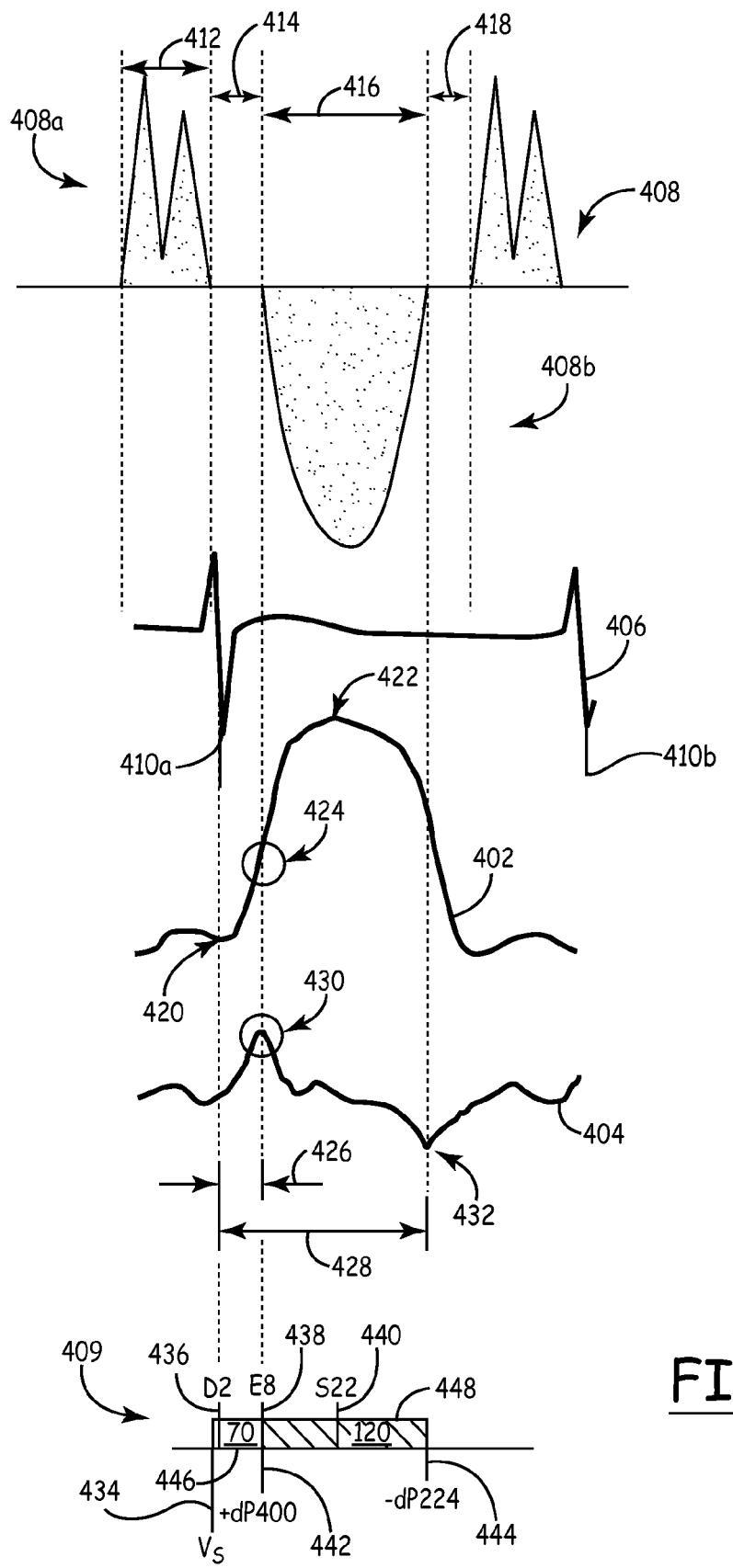
FIG. 4 is a diagram that depicts a right ventricle pressure signal, various cardiac graphs, and a mechanical function marker signal.

Cardiac event marker process 300 employs a suitably configured cardiac RVP sensor to measure the RVP of the patient's heart (task 302). In this context, the RVP sensor is a type of mechanical characteristic sensor that generates a physiological data signal, namely, an RVP signal. The RVP signal is received at, and processed by, the host IMD (task 304). For instance, the raw RVP data may be processed and formatted for ease of analysis, and the IMD may generate the first derivative of the RVP signal to obtain the dRVP/dt signal (task 306). In this regard, FIG. 4 is a diagram that depicts an RVP signal 402, the associated dRVP/dt signal 404, the patient's EGM signal 406, and a corresponding mechanical function marker signal 409. For ease of description, FIG. 4 also depicts a composite valve flow signal 408. It should be appreciated that composite valve flow signal 408 (which includes a mitral valve inflow portion 408a above the baseline and an aortic valve outflow portion 408b below the baseline) represents a signal that could be obtained by external equipment, such as an electrocardiographic system, and that composite valve flow signal 408 need not represent a signal that is obtained from an implanted sensor or sensors. Composite valve flow signal 408 is shown here as an aid to better describe the timing of the mechanical cardiac events during a heartbeat cycle.

The various signals shown in FIG. 4 share a common horizontal time axis to better illustrate how certain cardiac events are related to one another. The time between the downward spikes 410 in EGM signal 406 represent one cardiac cycle (this interval is commonly known as the "RR interval" because it corresponds to the interval between two R waves in EGM signal 406). With reference to signal 408: the interval 412 represents the filling time (FT) of the right ventricle; the interval 414 represents the isovolumic contraction time (ICT), i.e., the time during which the left ventricle is contracting but the valve has not yet opened; the interval 416 represents the ejection time (ET) of the right ventricle; and the interval 418 represents the isovolumic relaxation time (IRT). With reference to RVP signal 402: the right ventricle diastolic pressure (RVDP) 420 occurs at the time of downward spike 410a in EGM signal 406; the right ventricle systolic pressure (RVSP) 422 approximately corresponds to the maximum value of RVP signal 402; and the estimated pulmonary artery diastolic pressure (EPAD) 424 approximately corresponds to the beginning of the ET interval 416 in signal 408. Referring to dRVP/dt signal 404: the interval 426 represents the pre-ejection interval (PEI); and the interval 428 represents the systolic time interval (STI). Here, the PEI is measured from the downward spike 410a in EGM signal 406 to the point where dRVP/dt signal 404 is a maximum (reference number 430). Notably, the time of this maximum point 430 corresponds to the beginning of the ET interval 416 and to the time of the EPAD 424. In addition, the STI is measured from the downward spike 410a in EGM signal 406 to the point where dRVP/dt signal 404 is a minimum (reference number 432). The time of this minimum point 432 corresponds to the end of the ET interval 416.

Referring again to FIG. 3, cardiac function marker process 300 derives one or more cardiac function markers from attributes of the RVP signal and/or the dRVP/dt signal (task 308). For this embodiment, the IMD is suitably configured to derive event markers corresponding to one or more of the following detectable functional metrics, cardiac events, and durations: the PEI; the STI; the ET; and the EPAD. In practice, a given event marker may indicate a specific time or time period, along with a code or identifier that corresponds to the particular event that it marks. Although not a requirement, a given event marker may also convey magnitude and/or direction information that can be graphically rendered at a monitor device. The derived event markers can then be used to generate an appropriate cardiac event marker signal (task 310). In this embodiment, the IMD includes the processing capacity to generate the marker signal. The marker signal includes the event markers on a time scale such that the event markers can identify certain cardiac cycle timing characteristics for the patient. It should be appreciated that the marker signal can be generated in substantially real-time such that the patient's cardiac functions can be immediately monitored and interpreted.

FIG. 4 also depicts the marker signal 409 that corresponds to RVP signal 402. Marker signal 409 is one example of a mechanical marker channel (in contrast to conventional EGM-based electrical marker channels). For this embodiment, marker signal 409 includes markers associated with the following items: sensed electrical activity; EPAD; diastolic pressure; systolic pressure; maximum dRVP/dt for each cycle; and minimum dRVP/dt for each cycle. Marker signal 409 can be displayed at the external monitor device by itself or in conjunction with other signals, e.g., an EGM or ECG signal, RVP signal 402, an LVA signal, other event marker signals, or the like. In this regard, an external monitor device may be suitably configured to generate a superimposed display of more than one signal, graph, or plot. In certain embodiments, the monitor device and/or the IMD may be suitably configured to analyze RVP signal 402 and an EGM signal to determine cardiac electrical-mechanical coupling delay.

The sensed electrical activity is indicated by a marker 434 (for this example, a downward pointing line with the label "$V_S$"). The timing of marker 434 approximately corresponds to downward spike 410a in EGM signal 406, as depicted in FIG. 4. The diastolic pressure is indicated by a marker 436 (for this example, an upward pointing line with the label "D2"). The timing of marker 436 approximately corresponds to the occurrence of the RVDP 420 in RVP signal 402. The number included with marker 436 (the number two in this example) indicates the measured diastolic pressure value for the respective heartbeat. The EPAD is indicated by a marker 438 (for this example, an upward pointing line with the label "E8"). The timing of marker 438 approximately corresponds to the occurrence of the EPAD 424 in RVP signal 402. The number included with marker 438 (the number eight in this example) indicates the measured EPAD value for the respective heartbeat. The systolic pressure is indicated by a marker 440 (for this example, an upward pointing line with the label "S22"). The timing of marker 440 approximately corresponds to the occurrence of the maximum value of RVP signal 402. The number included with marker 440 (the number 22 in this example) indicates the measured systolic pressure value for the respective heartbeat. The maximum dRVP/dt is indicated by a marker 442 (for this example, a downward pointing line with the label "+dP400"). The timing of marker 442 approximately corresponds to the occurrence of the maximum point 430 in the dRVP/dt signal 404 for the respective heartbeat. The number included with marker 442 (the number 400 in this example) indicates the maximum dRVP/dt value for the respective heartbeat. The minimum dRVP/dt is indicated by a marker 444 (for this example, a downward pointing line with the label "−dP224"). The timing of marker 444 approximately corresponds to the occurrence of the minimum point 432 in the dRVP/dt signal 404 for the respective heartbeat. The number included with marker 444 (the number 224 in this example) indicates the minimum dRVP/dt value for the respective heartbeat. As shown in FIG. 4, the various markers in marker signal 409 are all arranged on a horizontal time scale that corresponds to the horizontal time scale of RVP signal 402 and dRVP/dt signal 404.

In this embodiment, marker signal 409 includes a field 446 that indicates the pre-ejection time in milliseconds (70 milliseconds for this example). This field 446 is displayed with the respective time value to enable the user to quickly interpret this portion of marker signal 409. In addition, this field 446 may be coded with a designated color, shade, or pattern to make it easily distinguishable in marker signal 409. In this embodiment, marker signal 409 also includes a field 448 that indicates the ejection time in milliseconds (120 milliseconds for this example). This field 448 is displayed with the respective time value to enable the user to quickly interpret this portion of marker signal 409. In addition, this field 448 may be coded with a designated color, shade, or pattern to make it easily distinguishable in marker signal 409. For example, field 446 can be colored green and field 448 can be colored blue. Such color, shade, or pattern coding can be used to indicate other physiologic/pathologic ranges for different cardiac conditions.

Referring back to FIG. 3, the IMD can transmit the cardiac event marker signal to an external device, such as an external monitor device (task 312). As explained above, the IMD and the external device are suitably configured to support a given wireless telemetry protocol that enables wireless data exchange. The monitor device can then process the received event marker signal, process it, and render an appropriate graphical representation of the event marker signal for display to a user (task 314). As mentioned previously, in certain embodiments the external device also displays the patient's EGM signal concurrently with the event marker signal. Such a combined display can be helpful for purposes of interpreting the displayed signals. Moreover, the event markers and/or the event marker signal may be used to calculate one or more common cardiac performance indices, such as: Tei index; Z-ratio; and MPI. In this regard, the Tei index or MPI can be calculated using the following relationships:

$$Tei = \frac{ICT - IRT}{ET} \text{ or } Tei = \frac{PEI \times 2}{STI - PEI}$$

(the variables in these relationships were described above). The Z-ratio can be calculated using the following relationships:

$$Z = \frac{FT + ET}{FT + ICT + ET + IRT} \text{ or } Z = \frac{RRI - (PEI \times 2)}{RRI},$$

where RRI is the R-R interval taken from an EGM signal, and where the other variables are as described above. FIG. 3 depicts task 314 leading back to task 302; this loop represents the ongoing and real-time nature of cardiac event marker process 300.

Figure 5:
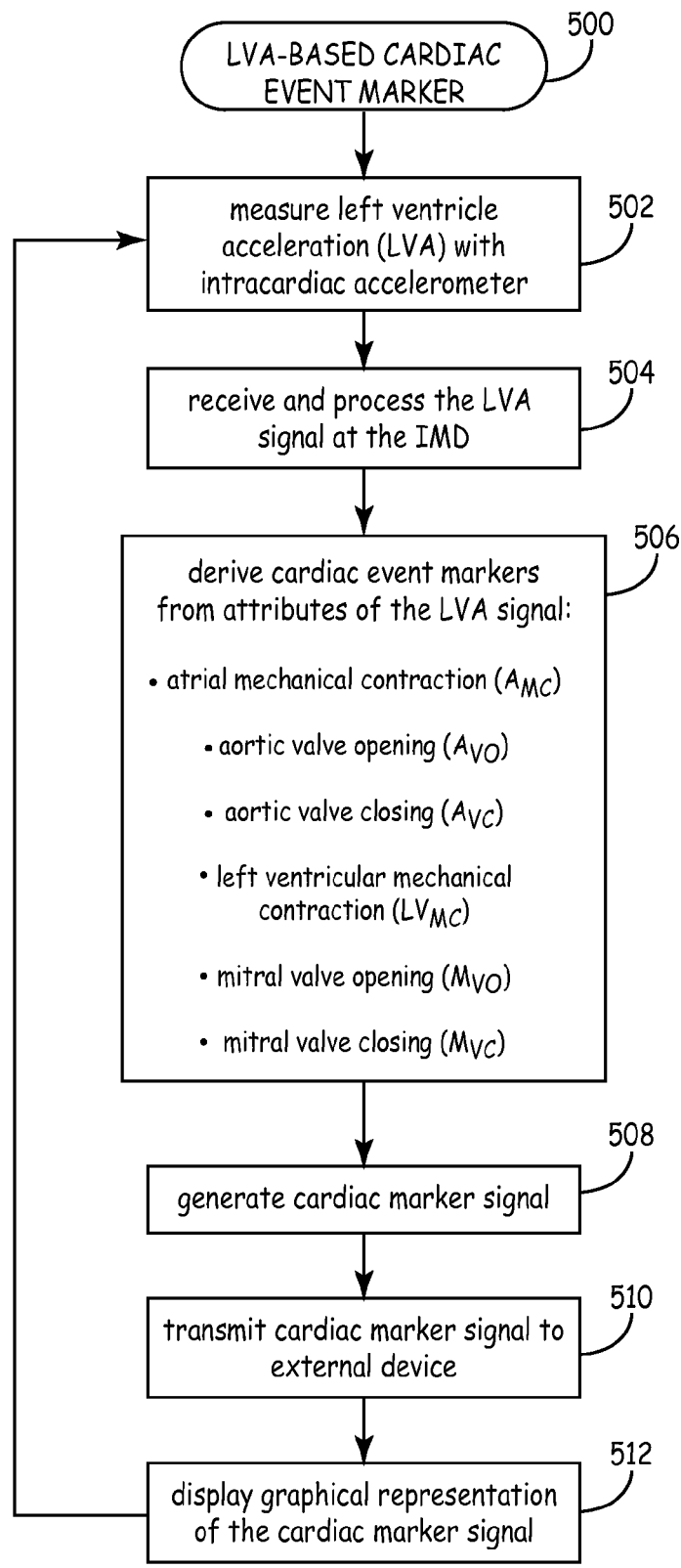
FIG. 5 is a flow chart that illustrates an embodiment of a cardiac event marker process that utilizes left ventricle acceleration data.

FIG. 5 is a flow chart that illustrates an embodiment of a cardiac event marker process 500 that utilizes left ventricle acceleration data. The various tasks performed in connection with process 500 may be performed by software, hardware, firmware, or any combination thereof. For illustrative purposes, the following description of process 500 may refer to elements mentioned above in connection with FIG. 1 and FIG. 2. In practice, portions of process 500 may be performed by different elements of the described system, e.g., implanted sensors, an IMD, or an external monitoring device. It should be appreciated that process 500 may include any number of additional or alternative tasks, the tasks shown in FIG. 5 need not be performed in the illustrated order, and process 500 may be incorporated into a more comprehensive procedure or process having additional functionality not described in detail herein. A number of features, characteristics, and tasks associated with process 500 are similar or identical to those described above for process 300. For the sake of brevity, such shared features, characteristics and tasks will not be redundantly described here in the context of process 500.

Cardiac event marker process 500 employs a suitably configured cardiac accelerometer to measure the LVA of the patient's heart (task 502). In this context, the accelerometer is a type of mechanical characteristic sensor that generates a physiological data signal, namely, an LVA signal. The LVA signal is received at, and processed by, the host IMD (task 504). For instance, the raw LVA data may be processed and formatted for ease of analysis, and the IMD may derive a number of cardiac event markers from the LVA signal (task 506). In this regard, FIG. 6 is a diagram that depicts an LVA signal 600 and a corresponding event marker signal 602.

LVA signal 600 and event marker signal 602 share a common horizontal time axis to better illustrate how the event marker signal 602 indicates timing characteristics of LVA signal 600. LVA signal 600 is characterized by a number of events/intervals, which are approximately defined by waveform traits such as: the absolute maximum within a heart cycle; the absolute minimum within a heart cycle; local maxima within a heart cycle; local minima within a heart cycle; waveform shapes within a heart cycle; waveform slopes; or the like. For example, LVA signal 600 is partitioned in a manner that indicates the following events and intervals: ET 604; IRT 606; passive filling 608; diastases 610; active filling 612; and ICT 614. Here, passive filling, diastases, and active filling together approximately correspond to the FT interval 412 depicted in FIG. 4. These events normally correspond to a single heartbeat cycle and, therefore, the sequence of events repeats as depicted in FIG. 6.

The ET interval 604 generally corresponds to the M-shaped waveform that is defined between downward spikes 616 and 618. As shown in FIG. 6, this M-shaped waveform can be easily detected in each heartbeat cycle. Downward spike 618 also serves as the demarcation point for the beginning of IRT interval 606. The end of IRT interval 606, which may overlap with passive filling interval 608, typically occurs between downward spike 620 and upward spike 622. In practice, the actual endpoint of IRT interval 606 may fluctuate relative to downward spike 620 and/or upward spike 622 and, therefore, suitable estimation and approximation techniques may be implemented. Passive filling interval 608 generally corresponds to the W-shaped waveform that includes downward spike 620, the downward sloping leg before downward spike 620, upward spike 622, and downward spike 624. The endpoint of this W-shaped waveform is defined by upward spike 626. As shown in FIG. 6, this W-shaped waveform can be easily detected in each heartbeat cycle. Diastases 610 (i.e., a brief period when the heart remains still) occurs between passive filling interval 608 and active filling interval 612. Diastases 610 typically corresponds to a brief valley 628 that occurs between upward spike 626 and upward spike 630. In practice, it may be difficult to precisely identify diastases 610 from LVA signal 600 and, therefore, suitable estimation and approximation techniques may be implemented. Active filling interval 612 generally corresponds to the downward slope that occurs between upward spike 630 and downward spike 632, which is easily detected in LVA signal 600. The ICT interval 614 generally corresponds to the waveform that is defined between downward spike 630 and upward spike 634. The waveform for ICT interval 614 resembles a letter M that has been horizontally compressed and vertically misaligned.

Referring again to FIG. 5, cardiac event marker process 500 derives one or more cardiac event markers from attributes of the LVA signal (task 506). For this embodiment, the IMD is suitably configured to derive event markers corresponding to one or more of the following detectable cardiac events: atrial mechanical contraction ($A_{MC}$); aortic valve opening ($A_{VO}$); aortic valve closing ($A_{VC}$); left ventricular mechanical contraction ($LV_{MC}$); mitral valve opening ($M_{VO}$); and mitral valve closing ($M_{VC}$). In practice, a given event marker may indicate a specific time or time period, along with a code or identifier that corresponds to the particular event that it marks. Although not a requirement, a given event marker may also convey magnitude and/or direction information that can be graphically rendered at a monitor device. The derived event markers can then be used to generate an appropriate cardiac event marker signal (task 508), which is transmitted from the IMD to an external monitor device (task 510) for display at the monitor device (task 512). Tasks 508, 510, and 512 are similar to respective tasks 310, 312, and 314 described above for cardiac event marker process 300.

FIG. 6 also depicts the event marker signal 602 that corresponds to LVA signal 600. Event marker signal 602 is one example of a mechanical marker channel (in contrast to conventional EGM-based electrical marker channels). For this embodiment, event marker signal 602 includes upward pointing $A_{VO}$ markers 636, upward pointing $A_{VC}$ markers 638, downward pointing $M_{VC}$ markers 640, downward pointing $M_{VO}$ markers 642, upward pointing $A_{MC}$ interval markers 644, and downward pointing $LV_{MC}$ interval markers 646, all arranged on a horizontal time scale that corresponds to the horizontal time scale of LVA signal 600. Event marker signal 602 can be displayed at the external monitor device by itself or in conjunction with other signals, e.g., an EGM or ECG signal, LVA signal 600, an RVP signal, other event marker signals, or the like. In this regard, an external monitor device may be suitably configured to generate a superimposed display of more than one signal, graph, or plot. In certain embodiments, the monitor device and/or the IMD may be suitably configured to analyze LVA signal 600 and an EGM signal to determine cardiac electrical-mechanical coupling delay.

$A_{VO}$ marker 636 indicates the opening of the aortic valve and, therefore, $A_{VO}$ marker 636 generally corresponds to downward spike 616 in LVA signal 600. $A_{VC}$ marker 638 indicates the closing of the aortic valve, and, therefore, $A_{VC}$ marker 638 generally corresponds to downward spike 618 in LVA signal 600. For this embodiment, event marker signal 602 includes a field 648 that indicates the ejection time in milliseconds (418 milliseconds for this example). This field 648 is displayed with the respective time value to enable the user to quickly interpret this portion of event marker signal 602. $M_{VO}$ marker 642 indicates the opening of the mitral valve and, therefore $M_{VO}$ marker generally corresponds to downward spike 620 in LVA signal 600. $M_{VC}$ marker 640 indicates the closing of the mitral valve and, therefore, $M_{VC}$ marker generally corresponds to downward spike 616 in LVA signal 600. For this embodiment, event marker signal 602 includes a field 650 that indicates the filling time in milliseconds (492 milliseconds for this example). This field 650 is displayed with the respective time value to enable the user to quickly interpret this portion of event marker signal 602.

$A_{MC}$ interval marker 644 indicates the time during which the atrium is mechanically contracting. Thus, $A_{MC}$ interval marker 644 is rendered as a pulse having a discernable width. Here, $A_{MC}$ interval marker 644 generally corresponds to active filling interval 612, which in turn is derived from LVA signal 600 as explained above. $LV_{MC}$ interval marker 646 indicates the time during which the left ventricle is mechanically contracting. Thus, $LV_{MC}$ interval marker 646 is rendered as a pulse having a discernable width. Here, $LV_{MC}$ interval marker 646 generally corresponds to ICT interval 614, which in turn is derived from LVA signal 600 as explained above.

The techniques and cardiac event marker signals described here provide additional cardiac information that was previously not obtainable in an effective and efficient manner. In particular, cardiac data based on mechanical characteristics of the heart (e.g., chamber pressure and/or wall acceleration) can now be used as a supplement to traditional EGM-based marker signals. Moreover, additional information can be derived from the raw mechanical sensor data, including, without limitation, velocity data, displacement data, and volume data. The techniques and event marker signals described here need not rely on imaging technologies such as echocardiograms or invasive surgical techniques.

While at least one example embodiment has been presented in the foregoing detailed description, it should be appreciated that a vast number of variations exist. It should also be appreciated that the example embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

The invention claimed is:

1. A method of obtaining information related to a cardiac cycle comprising:
   receiving a physiological data signal from a mechanical characteristic sensor, where the physiological data signal is indicative of a mechanical cardiac function;
   deriving cardiac event markers from attributes of the physiological data signal;
   generating a cardiac event marker signal using the cardiac event markers, the cardiac event marker signal identifying cardiac cycle timing characteristics, wherein the cardiac event marker signal includes an indication of a duration of individual cardiac events of the cardiac cycle; and
   annotating the cardiac event marker signal with magnitude information associated with the mechanical function for graphical display of the cardiac event maker signal and the magnitude information.

2. The method of claim 1, further comprising transmitting the cardiac event marker signal to a device external to an implantable medical device.

3. The method of claim 1, wherein receiving a physiological data signal comprises receiving a heart wall acceleration signal from an accelerometer configured to measure acceleration of a heart wall.

4. The method of claim 3, wherein receiving the heart wall acceleration signal comprises receiving a left ventricular acceleration signal from the accelerometer.

5. The method of claim 4, wherein deriving cardiac event markers comprises deriving an atrial mechanical contraction event marker from the left ventricular acceleration signal.

6. The method of claim 4, wherein deriving cardiac event markers comprises deriving an aortic valve opening event marker from the left ventricular acceleration signal.

7. The method of claim 4, wherein deriving cardiac event markers comprises deriving an aortic valve closing event marker from the left ventricular acceleration signal.

8. The method of claim 4, wherein deriving cardiac event markers comprises deriving a left ventricular mechanical contraction event marker from the left ventricular acceleration signal.

9. The method of claim 4, wherein deriving cardiac event markers comprises deriving a mitral valve opening event marker from the left ventricular acceleration signal.

10. The method of claim 4, wherein deriving cardiac event markers comprises deriving a mitral valve closing event marker from the left ventricular acceleration signal.

11. The method of claim 1, wherein receiving a physiological data signal comprises receiving a heart chamber pressure signal from a pressure sensor configured to measure pressure within a heart chamber.

12. The method of claim 11, wherein receiving the heart chamber pressure signal comprises receiving a right ventricle pressure signal from the pressure sensor.

13. The method of claim 12, wherein deriving cardiac event markers comprises deriving a pre-ejection interval event marker from the right ventricle pressure signal.

14. The method of claim 12, wherein deriving cardiac event markers comprises deriving a systolic time interval event marker from the right ventricle pressure signal.

15. The method of claim 12, wherein deriving cardiac event markers comprises deriving, from the right ventricle pressure signal, an ejection time interval event marker that represents the ejection time of the right ventricle.

16. The method of claim 12, wherein deriving cardiac event markers comprises deriving an estimated pulmonary artery diastolic pressure event marker from the right ventricle pressure signal.

17. The method of claim 12, wherein deriving cardiac event markers comprises:
   generating a secondary signal based upon a first derivative of the right ventricle pressure signal; and
   deriving the cardiac event markers from attributes of the secondary signal.

18. The method of claim 1, further comprising receiving at least one additional physiological data signal from a physiological characteristic sensor, where the at least one additional physiological data signal is indicative of cardiac functionality, and where deriving cardiac event markers comprises deriving cardiac event markers from attributes of the physiological data signal and from attributes of the at least one additional physiological data signal.

19. The method of claim 1, wherein one or more of the cardiac event markers includes a code that indicates a mechanical cardiac event.

20. The method of claim 1, further comprising: receiving electrogram (EGM) signals from an electrical characteristic sensor; and deriving electrical markers that indicate the occurrence of cardiac electrical events based on the received EGM signals.

21. An implantable medical device (IMD) comprising:
a data collection module configured to obtain a physiological data signal indicative of mechanical cardiac functionality from a mechanical characteristic sensor;
a data processing module coupled to the data collection module, the data processing module being configured to derive cardiac event markers from attributes of the physiological data signal, and to generate a cardiac event marker signal using the cardiac event markers, the cardiac event marker signal identifying cardiac cycle timing characteristics and an indication of a duration of individual cardiac events, and wherein the data processing module derives magnitude information associated with the mechanical cardiac functionality; and
a communication module coupled to the data processing module, the communication module being configured to transmit the cardiac event marker signal and the magnitude information to a device external to the IMD.

22. The IMD of claim 21, further comprising an accelerometer coupled to the data collection module, the accelerometer being configured to measure acceleration of a heart wall, and to provide the physiological data signal as a heart wall acceleration signal.

23. The IMD of claim 21, further comprising a pressure sensor coupled to the data collection module, the pressure sensor being configured to measure pressure within a heart chamber, and to provide the physiological data signal as a heart chamber pressure signal.

24. The IMD of claim 21, wherein one or more of the cardiac event markers includes a code that indicates a mechanical cardiac event.

25. The IMD of claim 21, further comprising an electrical characteristic sensor, wherein the data collection module is configured to receive electrogram (EGM) signals from the electrical characteristic sensor, and wherein the data processing module is configured to derive electrical markers that indicate the occurrence of cardiac electrical events based on the received EGM signals.

26. An implantable medical device (IMD) system comprising:
a data collection module configured to obtain a physiological data signal indicative of mechanical cardiac functionality;
a data processing module coupled to the data collection module, the data processing module being configured to derive cardiac event markers from attributes of the physiological data signal, and to generate a cardiac event marker signal using the cardiac event markers, the cardiac event marker signal identifying cardiac cycle timing characteristics and durations of individual cardiac events, and wherein the data processing module derives magnitude parameters of the mechanical cardiac functionality; and
a communication module coupled to the data processing module, the communication module being configured to transmit the cardiac event marker signal and magnitude parameters to devices external to the IMD;
a mechanical characteristic sensor in communication with the IMD and configured to generate the physiological data signal in response to mechanical cardiac phenomena; and
a monitor device in communication with the IMD, the monitor device being configured to receive the cardiac event marker signal from the communication module, and to display a graphical representation of the cardiac event marker signal, wherein the graphical representation of the cardiac event marker signal is annotated with magnitude parameters for the mechanical cardiac functionality.

27. The IMD system of claim 26, wherein the mechanical characteristic sensor comprises an accelerometer coupled to the data collection module, the accelerometer being configured to measure acceleration of a heart wall, and to provide the physiological data signal as a heart wall acceleration signal.

28. The IMD system of claim 26, wherein the mechanical characteristic sensor comprises a pressure sensor coupled to the data collection module, the pressure sensor being configured to measure pressure within a heart chamber of the patient, and to provide the physiological data signal as a heart chamber pressure signal.

29. The IMD system of claim 26, the monitor device being configured to acquire an electrogram signal, and to display a graphical representation of the electrogram signal concurrently with the graphical representation of the cardiac event marker signal.

30. The IMD system of claim 29, the data collection module being configured to obtain the electrogram signal from electrodes coupled to the IMD, and the data processing module being configured to derive the cardiac event markers from attributes of the physiological data signal and attributes of the electrogram signal.

31. The IMD system of claim 26, the monitor device being configured to acquire an electrocardiogram signal for a patient, and to display a graphical representation of the electrocardiogram signal concurrently with the graphical representation of the cardiac event marker signal.

32. The IMD system of claim 26, wherein one or more of the cardiac event markers includes a code that indicates a mechanical cardiac event.

33. The IMD system of claim 26, further comprising an electrical characteristic sensor that obtains electrogram (EGM) signals, wherein the data collection module is configured to receive the EGM signals, wherein the data processing module is configured to derive electrical markers based on the EGM signals, and wherein the electrical markers indicate the occurrence of cardiac electrical events.

34. The IMD system of claim 33, further comprising a lead that includes the electrical characteristic sensor, wherein the lead is electrically coupled to the data collection module, and wherein the mechanical characteristic sensor is connected to the lead.

35. A method for obtaining information related to a cardiac cycle, the method comprising:
receiving a data signal from a mechanical characteristic sensor;
obtaining a cardiac mechanical function marker signal that identifies mechanical events associated with the cardiac cycle, wherein the cardiac mechanical function marker signal is based on the data signal and includes duration information indicating the length of occurrence of individual cardiac events;
obtaining an indication of magnitude of the mechanical cardiac functionality; and
displaying a graphical representation of the cardiac mechanical function marker signal, wherein the graphical representation includes annotations of the magnitudes of the mechanical cardiac functionality.

36. The method of claim 35, wherein displaying a graphical representation of the cardiac mechanical function marker signal comprises displaying an event marker indicative of mechanical events selected from the group consisting of:
- an atrial mechanical contraction event;
- an aortic valve opening event;
- an aortic valve closing event;
- a left ventricular mechanical contraction event;
- a mitral valve opening event;
- a mitral valve closing event;
- a pre-ejection interval event;
- a systolic time interval event;
- an ejection time interval event; and
- an estimated pulmonary artery diastolic pressure event.

37. The method of claim 35, wherein one or more of the cardiac event markers includes a code that indicates a mechanical cardiac event.

38. The method of claim 35, further comprising: receiving electrogram (EGM) signals from an electrical characteristic sensor; and deriving electrical markers that indicate the occurrence of cardiac electrical events based on the received EGM signals.

* * * * *